United States Patent [19]

Caulkett et al.

[11] Patent Number: 5,290,776
[45] Date of Patent: Mar. 1, 1994

[54] AZOLE DERIVATIVES

[75] Inventors: Peter W. R. Caulkett; Geraint Jones, both of Macclesfield; Michael G. Collis, Barham; Simon M. Poucher, Wilmslow, all of England

[73] Assignee: Imperial Chemical Industries, PLC, London, England

[21] Appl. No.: 886,798

[22] Filed: May 21, 1992

[30] Foreign Application Priority Data

Jun. 23, 1991 [GB] United Kingdom ............... 9111130

[51] Int. Cl.$^5$ ................... C07D 405/14; A51K 31/53
[52] U.S. Cl. .................................... 514/246; 514/245; 544/207; 544/209; 544/212; 544/217; 544/219
[58] Field of Search ............... 544/207, 212, 209, 217, 544/219; 514/246, 245

[56] References Cited

U.S. PATENT DOCUMENTS

| | | | |
|---|---|---|---|
| 3,846,423 | 11/1974 | Kobe et al. | 260/248 |
| 3,995,039 | 11/1976 | Rooney et al. | 424/249 |
| 4,133,674 | 1/1979 | Cartwright et al. | 71/93 |
| 4,560,689 | 12/1985 | Yokoyama | 514/250 |
| 4,713,383 | 12/1987 | Francis et al. | 514/267 |
| 4,734,413 | 3/1988 | Wade | 514/222 |

FOREIGN PATENT DOCUMENTS

| | | |
|---|---|---|
| 815405 | 11/1974 | Belgium . |
| 0172608 | 2/1986 | European Pat. Off. . |
| 0207651 | 1/1987 | European Pat. Off. . |
| 0217748 | 4/1987 | European Pat. Off. . |
| 0263071 | 4/1988 | European Pat. Off. . |
| 0374808 | 6/1990 | European Pat. Off. . |
| 0383589 | 8/1990 | European Pat. Off. . |
| 0459702 | 12/1991 | European Pat. Off. . |
| 2720792 | 11/1977 | Fed. Rep. of Germany . |
| 743316 | 7/1974 | South Africa . |
| 2016002 | 9/1979 | United Kingdom . |
| 2134107 | 8/1984 | United Kingdom . |

OTHER PUBLICATIONS

W. Ried, S. Aboul-Fetouh "Synthesis of new Substituted Pyrazolo[1,4-a]pyrimidines and Pyrazolo[1,5-a]-1,3,5-Triazines" *Tetrahedron* (1988), 44, 7155–7162.

J. P. Miller, et al. "Inhibition of Cyclic AMP Phosphodiesterases by Cyclic Nucleotide Analogs and Nitrogen Heterocycles" *Advances in Cyclic Nucleotide and Protein Phosphorylation Research* (1984), 16, 277–290.

K. Senga, et al. "Synthesis and Enzymic Acitivity of Various Substituted Pyrazolo-[1,5-a]-1,3,5-triazines as (List continued on next page.)

Primary Examiner—John M. Ford
Attorney, Agent, or Firm—Cushman, Darby & Cushman

[57] ABSTRACT

A compound of the formula I

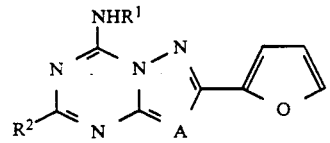

wherein:

$R^1$ is hydrogen, (1-6C)alkyl, or (1-4C)alkanoyl;

$R^2$ is phenyl, a C-linked aromatic 5- or 6-membered heterocyclic ring containing one of oxygen and sulphur and/or one or two nitrogen, or (1-8C)alkyl, alkenyl or alkynyl unsubstituted or substituted by a phenyl or a C-linked aromatic 5- or 6-membered heterocylic ring containing one of oxygen and sulphur and/or one or two nitrogen, any phenyl being unsubstituted or substituted by one, two or three of (1-4C)alkyl, (1-4C)alkoxy, halogen, trifluoromethyl, hydroxy, benzyloxy and (1-5C)alkanoyloxy;

A is N or CT in which T is hydrogen or (1-4C)alkyl;

or a pharmaceutically acceptable salt thereof, processes for the manufacture of the compounds, and pharmaceutical compositions containing them. The compounds are useful as adenosine antagonists.

8 Claims, No Drawings

OTHER PUBLICATIONS

Adensoine Cyclic 3′,5′-Phosphate Phosphodiesterase Inhibitors" *J. Med Chem* (1982), 25, 243–249.

G. Griebel, et al. "Behavioural effects of Selective $A_2$ Adenosine Receptor Antagonists, CGS 21197 and CGS 22706, in Mice" *NeuroReport* (1991), 2, 139–140.

S. P. Langdon, et al. "Triazines and Related Products. Part 26. Synthesis and Chemistry of Bicyclic Analogs of Antiiumor Drug 2,4,6–Tris(dimethylamino)-1,3,5-triazine (Hexamethylmelamine)" *J. Chem. SOC., Perkin Trans I* (1984), 993–998.

Callis, et al. "Inhibition of Renal Vasoconstriction Induced by Intrarenal Hypertonic Sailne by the Nonxanthine Adenosine Antagonist CGS 1594A" *J. Pharmacol Exp. Therap* (1989), 248 (3), 1123–1129.

E. B. Akerblom, D. E. S. Campbell "Nitrofuryltriazole Derivatives as Potential Urinary Tract Antibacterial Agents" *J. Med. Chem.* (1973), 16(4) 312–319.

AZOLE DERIVATIVES

This invention concerns novel azole derivatives and, more particularly, certain 2-furyl-triazolo[1,5-a][1,3,5]triazines and pyrazolo[2,3-a][1,3,5-]triazines which have useful pharmacological properties (and in particular antagonise the actions of adenosine such as vasodilation). The invention also includes pharmaceutical compositions containing the novel azole derivatives for use in treating certain diseases and disorders affecting mammalian cardiac, peripheral and/or cerebral vascular systems. Also included are processes for the manufacture and formulation of the novel azole derivatives.

The compound theophylline (1,3-dimethylxanthine) has been used clinically (usually as its ethylene diamine salt, which is also known as aminophylline) as a respiratory stimulant, a centrally acting stimulant, a bronchodilator, a cardiac stimulant and as a diuretic. This diversity of clinical uses is an indication of the range of pharmacological actions which have been attributed to theophylline. These include phosphodiesterase inhibition, adenosine receptor antagonism, mobilisation of intracellular calcium and the release of catecholamines. Recently theophylline has also been reported to be useful in treating myocardial ischaemia (Maseri et al., *The Lancet*, 1989, 683–686), skeletal muscle ischaemia (Picano et al., *Angiology*, 1989, in press) and cerebral ischaemia (Skinhoj et al., *Acta. Neurol. Scand.*, 1970, 46, 129–140). The beneficial effects of theophylline in these ischaemic disorders are believed to be due to a reduction or prevention of the phenomenon known as "vascular steal" by virtue of the compound's ability to antagonise the actions of adenosine by blocking the adenosine receptors which mediate metabolism-linked vasodilatation.

The "vascular steal" phenomenon can occur when the major artery supplying a particular vascular bed is partially or totally occluded resulting in ischaemia. In this situation, the compromised vascular bed dilates and blood flow is maintained by either an increase in flow across the narrowed vessel or by an increase in flow through the collateral vessels. However, increased metabolic activity in adjacent vascular beds results in release of mediators such as adenosine, causing them to dilate, resulting in the limited blood flow to the compromised vascular bed being "stolen" by these adjacent areas. The loss of blood from compromised to normally perfused vascular beds by the phenomenon of "vascular steal" further diminishes the blood flow in the compromised vascular bed.

The diversity of pharmacological properties possessed by theophylline make it difficult to use in the regular treatment or prevention of occlusive diseases and conditions of the vasculature. Thus, its associated action as a phosphodiesterase inhibitor results in cardiac stimulation which is deleterious for patients with myocardial ischaemia. Furthermore, the relatively low potency of theophylline means that dose-levels which are therapeutically useful are close to those which can cause serious central side-effects.

European patent application publication no. EP A2 383589 discloses the formulae of certain 2-furyl-pyrazolo[2,3-a][1,3,5]triazines, although no details of their preparation are given. No therapeutic use is ascribed to any of these compounds.

Several traizolo[1,5-a][1,3,5]triazines and pyrazolo[2,3-a][1,3,5]triazines which do not have a 2-furyl substituent have been ascribed therapeutic uses. Thus, certain triazolo[1,5-a][1,3,5]triazines have been disclosed as bronchodilators (see U.S. Pat. No. 4,734,413). Certain pyrazolo[2,3-a][1,3,5]triazines have been disclosed variously as inhibitors of gastric acid secretion (see British patent application publication no. 2134107 and European patent application publication no. EP A2 0172608); as antiinflammatory agents (see European patent applications publication nos. EP A2 0172608 and EP A2 207651); as bronchodilators (see British patent application publication no. GB 2016002, Belgian patent application publication no. 815405 and U.S. Pat. No. 3,995,039), and as phosphodiesterase inhibitors (see U.S. Pat. No. 3,846,423 and J. Med. Chem., 1982, 25(3), 243-9).

European patent application publication number EP A1 459702, published on Dec. 4th, 1991, discloses certain 2-heteroaryltriazolo[1,5-a][1,3,5]triazines and pyrazolo[2,3-a][1,3,5]triazines having adenosine antagonist activity.

We have now discovered (and this is a basis for our invention) that a group of novel 2-furyl-triazolo[1,5-a][1,3,5]triazines and pyrazolo[2,3-a][1,3,5]triazines of formula I defined below are effective antagonists of the actions of adenosine and in particular of its vasodilatory actions.

According to the invention there is provided a compound of the formula I set out hereinafter (together with the other formulae appearing in Roman numerals) wherein:

$R^1$ is hydrogen, (1–6C)alkyl, or (1–4C)alkanoyl;

$R^2$ is phenyl, a C-linked aromatic 5- or 6-membered heterocylic ring containing one of oxygen and sulphur and/or one or two nitrogen, or (1–8C)alkyl, alkenyl or alkynyl unsubstituted or substituted by a phenyl or C-linked aromatic 5- or 6-membered heterocyclic ring containing one of oxygen and sulphur and/or one or two nitrogen, any phenyl being unsubstituted or substituted by one, two or three of (1–4C)alkyl, (1–4C)alkoxy, halogen, trifluoromethyl, hydroxy, benzyloxy and (1–5C)alkanoyloxy;

A is N or CT in which T is hydrogen or (1–4C)alkyl; or a pharmaceutically acceptable salt thereof.

It will be appreciated that certain of the compounds of formula I may exist in and be isolated in one or more different enantiomeric or racemic forms (or mixtures thereof). It is to be understood that the invention includes any of such forms which possesses the property of antagonising the actions of adenosine, it being well known how to prepare individual enantiomeric forms, for example, by synthesis from appropriate chiral starting materials or by resolution of a racemic form. Similarly, the adenosine antagonist properties of a particular form may be readily evaluated, for example by use of one or more of the standard in vitro or in vivo screening tests detailed hereinbelow.

$R^1$ may be, for example, hydrogen, methyl or acetyl. Preferably $R^1$ is hydrogen.

When $R^2$ is (1–8C)alkyl, alkenyl or alkynyl, this may be unbranched or branched. Preferably it is unbranched. A substituted (1–8C)alkyl, alkenyl or alkynyl is preferably terminally substituted. When $R^2$ is alkenyl or alkynyl, it is preferably connected to the 5-position of the triazine ring directly through the double or triple bond. An alkenyl may be in the (E) or (Z) configuration.

Particular examples of (1–8C)alkyl, alkenyl or alkynyl groups are:

for alkyl: methyl, ethyl, propyl, butyl, pentyl and hexyl;

for alkenyl: ethenyl, propenyl, butenyl, pentenyl and hexenyl; and for alkynyl: ethynyl, propynyl, butynyl, pentynyl and hexynyl.

Preferably $R^2$ is a group of formula $R^3(CH_2)_nX_m$ in which n is 0 or an integer of from 1 to 6; m is 0 or 1; X is HC=CH or C≡C; and $R^3$ is phenyl unsubstituted or substituted by one, two or three of (1–4C)alkyl, (1–4C)alkoxy, halogen, trifluoromethyl, hydroxy, benzyloxy and (1–5C)alkanoyloxy, or a C-linked aromatic 5- or 6-membered heterocylic ring containing one of oxygen and sulphur and/or one or two nitrogen, or when n is greater than 0, hydrogen.

Particular examples of substituents which may be present on phenyl are:

for (1–4C)alkyl: methyl or ethyl;

for (1–4C)alkoxy: methoxy or ethoxy;

for halogen: fluorine and chlorine; and for (1–5C)alkanoyloxy: pivaloyloxy.

Examples of unsubstituted and substituted phenyl groups include: phenyl, 2-methylphenyl, 4-methylphenyl, 4-methoxyphenyl, 3-fluorophenyl, 4-fluorophenyl, 3,5-difluorophenyl, 3-trifluoromethyl, 4-trifluoromethylphenyl, 4-hydroxyphenyl, 4-benzyloxyphenyl and 4-pivaloyloxyphenyl.

Particular examples of a C-linked aromatic 5- or 6-membered heterocylic ring containing one of oxygen and sulphur and/or one or two nitrogen are thiophenyl, furyl, pyridyl and thiazolyl.

Particular examples for n are 0 and 2.

Examples of particular values for $R^2$ are phenyl, 3-trifluoromethylphenyl, 4-methoxyphenyl, 4-methylphenyl, 3-fluorophenyl, 3,5-difluoromethyl, thiophenyl, 4-benzyloxybenzyl, hex-1-ynyl, but-3-enyl, 2-phenylethynyl, 2-phenylethyl and 3-phenylpropyl.

A may be, for example, N or CT in which T is hydrogen or methyl. Preferably A is N or CH.

Particular pharmaceutically acceptable salts include, for example, salts with acids affording physiologically acceptable anions, for example, salts with strong acids, such as hydrochloric, hydrobromic, sulphuric, phosphoric, methanesulphonic and trifluoracetic acids. In addition, for those compounds of formula I which are sufficiently basic, suitable salts include, for example, salts with organic acids affording a physiologically acceptable anion such as salts with oxalic, citric or maleic acid. Certain compounds of formula I, for example those in which $R^2$ comprises a phenol group, may form base salts with bases affording physiologically acceptable cations, such as alkali metal and alkaline earth metal salts.

The compounds of formula I may be manufactured using procedures analogous to those well known in the arts of heterocyclic and organic chemistry for the production of structurally analogous compounds. Such procedures are included as a further feature of the invention and include the following preferred procedures for the manufacture of a compound of the formula I in which $R^1$, $R^2$, and A have any of the meanings defined above:

(a) The reaction of a compound of the formula II in which Z is a suitable leaving group, for example hydrocarbylsulphonyl such as (1–6C)alkylsulphonyl (such as methylsulphonyl or ethylsulphonyl), or halogeno (such as chloro, bromo or iodo), with an appropriate organometallic reagent (such as a Grignard reagent of the formula $R^2MgY$ in which Y is a halogen atom (such as chlorine, bromine or iodine).

The process is conveniently carried out at a temperature in the range, for example, 10° to 120° C. and conveniently in the range 15° to 80° C. and in a suitable solvent or diluent such as an ether, e.g., diethylether or tetrahydrofuran. It is particularly effective for preparing compounds of formula I in which $R^2$ is an unsubstituted or substituted phenyl group.

The starting materials of formula II may be obtained by standard procedures well known in the art. Thus, for example, those compounds of formula II in which Z is alkylsulphonyl may be made by oxidation of the corresponding alkylthio derivative of formula III in which $R^4$ is (1–6C)alkylthio, using a conventional oxidant such as a peracid, for example, peracetic, perbenzoic or chloroperbenzoic acid, conveniently at a temperature in the range, for example, 0° to 40° C., and in a suitable solvent or diluent such as dichloromethane or chloroform. Similarly, those compounds of the formula II in which Z is chloro or bromo may be obtained, for example, by reacting an alkylthio derivative of formula III (especially in which $R^4$ is methylthio or ethylthio) with chlorine or bromine in the presence of hydrogen chloride or hydrogen bromide, respectively, at a temperature in the general range, for example, −20° to 15° C. and in a generally inert polar solvent such as ethanol or 2-propanol.

When a Grignard reagent of formula $R^2MgY$ is used, this may conveniently be prepared in situ by reaction of a compound of formula $R^2Y$ with magnesium.

The starting alkylthio starting materials of formula III may themselves be obtained, for example, by reaction of a compound of the formula IV with the appropriate dialkyl N-cyanodithioiminocarbonate of formula V, in which $R^4$ has any of the meanings defined above, at elevated temperature in the range, for example, 60° to 200° C., conveniently as a melt in the absence of solvent or diluent, to give the compound of formula III in which $R^1$ is hydrogen. When a compound of formula I in which $R^1$ is alkyl is required, the compound of formula III in which $R^1$ is hydrogen may be alkylated or acylated in conventional manner.

It will be understood that in some circumstances, when A is N, some of the isomeric 7-alkylthio-5-amino compound of formula VI may also be obtained during the reaction of the formula IV and V compounds and that this material may be separated by conventional procedures, for example by chromatography.

The starting compounds of formula IV wherein A is N may themselves be obtained, for example by reacting the appropriate iminoether of formula VII in which R is (1–4C)alkyl such as methyl or ethyl (formed from 2-furonitrile and an alcohol of the formula R.OH in the presence of an anhydrous acid such as hydrogen chloride) with an aminoguanidine salt (especially the nitrate) in the presence of a suitable base, such as pyridine or 2,6-lutidine, which may also be used as the reaction solvent, at a temperature in the range, for example, 60°–120° C.

The starting compounds of formula IV wherein A is CT may themselves be obtained, for example by reacting the appropriate ester of formula VIII (in which R is lower alkyl such as methyl or ethyl) under basic conditions with an alkali metal salt of the formula T.CHM.CN (in which M is an alkali metal such as sodium or lithium), conveniently produced in situ by adding a nitrile of the formula T.CH$_2$.CN to a solution of the alkali metal in liquid ammonia, to give the corresponding cyanoalkylketone of the formula IX. The latter compound is then cyclised with hydrazine, for example by heating in a suitable solvent or diluent such as ethanol or propanol to give the required pyrazole of formula IV.

(b) A compound of the formula IV is reacted at elevated temperature with a compound of formula X in which Za is a leaving group (such as a (1–6C)alkylthio group, for example methylthio).

The process is generally performed at a temperature in the general range, for example, 60° to 200° C. and may be performed in the absence of any solvent or diluent. Otherwise any conventional solvent or diluent may conveniently be used which is generally inert and of adequate boiling point. It will be appreciated that, under certain circumstances when A is N, for example when the reaction is performed at temperatures only slightly above room temperature, it may be possible to produce significant quantities of the thermodynamically less stable, isomeric [1,2,4]triazolo[4,3-a][1,3,5]triazine derivative of the formula XI, and this isomeric material may be separated by conventional procedures such as chromatography.

The compounds of formula X may be prepared according to the method described in Arch. Pharm. (Weinheim), 303(8), 625–33.

(c) The invention accordingly provides a further process for preparing a compound of formula I in which A is N, in which a [1,2,4]triazolo[4,3-a][1,3,5]triazine derivative of the formula XI is rearranged.

The rearrangement is generally carried out by heating the compound of formula XI in a suitable solvent or diluent, for example, a (1–6C)alkanol, such as ethanol, 2-propanol or butanol, at a temperature in the general range, for example, 60° to 140° C. The rearrangement may optionally be carried out in the presence of an acid or base catalyst, for example an alkali metal alkoxide or hydroxide such as sodium hydroxide.

The starting materials of formula XI may be obtained, for example, as described in connection with (b) above.

(d) For those compounds of formula I in which R$^2$ comprises a hydroxyphenyl moiety, a corresponding derivative of formula I in which the hydroxy group is protected, for example with a benzyl group, is deprotected.

It will be appreciated that compounds of formula I in which R$^2$ comprises a hydroxyphenyl moiety include those wherein R$^2$ is hydroxyphenyl and those wherein part of R$^2$ is hydroxyphenyl, as for example in a hydroxyphenylalkyl group.

The protecting group and deprotection conditions are those well known in the art for use with hydroxy groups and which are compatible with the presence of other reactive groups in the formula I compound. Thus, for example, a benzyl group may be removed by hydrogenation in the presence of a suitable catalyst such as palladium-on-carbon at or about atmospheric pressure of hydrogen in a suitable inert diluent or solvent such as methanol, ethanol or t-butyl methyl ether and at or about ambient temperature.

The protected derivatives of formula I may in general be made using analogous procedures to processes (a)–(c) and (e) herein but starting from the appropriately protected starting materials.

(e) For the preparation of a compound of formula I in which R$^2$ is an unsubstituted or substituted alkynyl group (such as a group of formula R$^3$(CH$_2$)$_n$C≡C), a compound of formula II in which Z is iodine is reacted with an appropriate alkyne (such as a compound of formula R$^3$(CH$_2$)$_n$C≡CH) in the presence of a palladium catalyst.

Suitable palladium catalysts include those comprising a palladium (II) salt, for example palladium (II) acetate or palladium (II) chloride; a phosphine such as triphenylphosphine; and optionally a tertiary amine such as triethylamine, and/or cuprous iodide.

The reaction is conveniently performed at a temperature in the range of from 0° to 100° C., preferably from 10° to 40° C. Suitable solvents for the reaction include amides such as dimethylformamide.

(f) For those compounds of formula I in which A is N and R$^1$ is hydrogen or (1–6C)alkyl, a compound of formula XII in which Zb is a suitable leaving group, for example aryloxy (such as phenoxy), alkylthio (such as methylthio) or halogeno (such as chloro or bromo) is reacted with a compound of formula R$^1$NH$_2$.

The process is conveniently effected at a temperature in the range of, for example, from 0° to 100° C. Suitable solvents for the process include alcohols such as ethanol and ethers such as tetrahydrofuran. When R$^1$ is hydrogen, it is particularly convenient to employ a solution of ammonia in an alcohol, such as ethanol, at ambient temperature.

The compounds of formula XII in which R$^2$ is an unsubstituted or substituted (1–8C)alkynyl may be obtained by reacting a compound of formula XIII with an alkyne in the presence of a palladium catalyst according to the method of process (e) hereinbefore.

Compounds of formula XII in which R$^2$ is an unsubstituted or substituted (1–8C)alkyl or alkenyl may be prepared by hydrogenating the corresponding compound of formula XII in which R$^2$ is an unsubstituted or substituted (1–8C)alkynyl group using a conventional method, for example using palladium on carbon.

The compounds of formula XIII may be prepared by reacting a compound of formula VI (which may be prepared as described hereinbefore) in which A is N with diiodomethane and amyl nitrite. The reaction is conveniently effected at a temperature of from 50° to 150° C. in a suitable solvent such as dichloromethane.

The compounds of formula XII may alternatively be prepared by dehydrating a compound of formula XIV. Suitable dehydrating agents include, for example, phosphorous pentoxide or a sulphonyl chloride such as p-toluenesulphonyl chloride. The dehydration is conveniently effected at a temperature in the range of from 60° to 180° C. When phosphorus pentoxide is used, convenient solvents include the aromatic hydrocarbons such as xylene or toluene. When a sulphonyl chloride is used, convenient solvents include tertiary amines such as pyridine.

The compounds of formula XIV may be obtained by reacting a compound of formula XV with a 2-halocarbonylfuran, such as 2-chlorocarbonylfuran. The reaction may conveniently be effected at a temperature in the range of from −10° to 40° C. Suitable solvents for the reaction include halogenated hydrocarbons such as dichloromethane.

The compounds of formula XV may be obtained by reacting a compound of formula XVI in which Zc is a leaving group with hydrazine.

Alternatively, the compounds of formula XII may be obtained by reacting a compound of formula XVI with a compound of formula XVII.

The compounds of formula XVI may be prepared according to the methods described in Synthesis, (11), 907-8, 1981 and Synthesis (1), 40-2, 1978.

It will be appreciated that those compounds in which $R^1$ is other than hydrogen may also be obtained by carrying out a conventional alkylation or acylation of the corresponding formula I compound in which $R^1$ is hydrogen obtained by one of processes (a)-(f) above.

It will also be appreciated that those compounds of formula I in which $R^2$ contains an acyloxy group, for example where $R^2$ is (1-5C)alkanoyloxyphenyl or (1-5C)alkanoyloxyphenyl(1-8C)alkyl, may be prepared by acylating the corresponding compounds of formula I in which $R^2$ comprises a hydroxy group, as for example where $R^2$ is hydroxyphenyl or hydroxyphenyl(1-8C)alkyl. The acylation may be conducted by reaction with any conventional acylating agent, for example a (1-5C)alkanoyl halide or (1-5C)alkanoic acid anhydride.

Compounds of formula I in which $R^2$ is an unsubstituted or substituted alkyl or alkenyl group may conveniently be prepared by hydrogenating a corresponding compound in which $R^2$ is alkenyl or alkynyl in a conventional manner, for example using palladium on carbon as catalyst.

Whereafter, when a pharmaceutically acceptable salt is required, it may be obtained, for example, by reacting a compound of formula I with the appropriate acid or base affording a physiologically acceptable ion or another conventional procedure.

Similarly, when an optically active form of a chiral compound of formula I is required, either one of processes (a)-(f) above may be carried out using the appropriate optically active starting material or else a racemic form may be resolved by a conventional procedure, for example, using an optically active form of a suitable acid.

Certain of the starting materials used in the processes according to the invention are novel, and these are provided as further aspects of the invention. For example, the invention provides compounds of formula XI in which $R^1$ and $R^2$ are as defined hereinabove. The invention also provides compounds of formula XII in which $R^2$ and Zb are as defined hereinabove.

As stated above, the compounds of the invention possess the property of antagonising one or more of the physiological actions of adenosine and are valuable in the treatment of diseases and medical conditions affecting the mammalian cardiac, peripheral and/or cerebral vascular systems, such as ischaemic heart disease, peripheral vascular disease (claudication) and cerebral ischaemia. The compounds may also be useful in the treatment of migraine.

The effects of compounds of formula I as adenosine receptor antagonists may be demonstrated in one or more of the following standard in vitro and/or in vivo tests.

(a) $A_2$ Adenosine receptor affinity test

This test involves the ability of a test adenosine antagonist to displace the known adenosine mimetic agent [$^3$H]-N-ethylcarboxamidoadenosine (NECA) from binding sites on membrane preparations derived from the rat phaeochromocytoma cell line PC 12 (available from the Beatson Institute, Glasgow). The basic procedure has been described by Williams et al. (J. Neurochemistry, 1987, 48(2), 498-502).

The membrane preparation is obtained as follows: Frozen pellets of PC12 cells are washed twice with ice cold, buffered, physiological saline and the cells recovered by centrifugation (1500 G) at 3° C. The separated cells are then suspended in hypotonic solution (distilled water), allowed to stand on ice for 30 minutes and are then carefully homogenized using a standard high-speed homogeniser with periodic ice-cooling to obtain a fine suspension. The homogenate is centrifuged (48000 G) and the pellet is resuspended in 50 mM tris-HCl buffer, pH 7.4 containing adenosine deaminase (5 units/ml, Type IV from calf intestinal mucosa, available from Sigma Chemical Corporation, under reference no. A1280). The mixture is then incubated at 37° C. After 20 minutes, the reaction is terminated by dilution with ice-cold buffer and transfer onto ice. The material obtained containing the cell membranes is recovered by centrifugation and washed by resuspension in buffer and recentrifugation. The pellet produced is then resuspended in ice-cold buffer using a hand-driven homogenizer. The resultant membrane suspension is frozen and stored under liquid nitrogen until required.

Binding studies are carried out in microtitre plates, the assay mixtures being buffered in 50 mM tris-HCl, pH 7.4 at room temperature. The test compound is dissolved in dimethyl sulphoxide (DMSO) and then diluted with assay buffer to give the test solutions. [The final concentration of DMSO is not allowed to exceed 1% by volume, at which level it does not affect radioligand binding to the membrane receptor.] Incubations are performed at 30° C. for 90 minutes in a total volume of 150 μl comprising the test solution or buffer (50 μl), tritiated NECA (50 μl) and membrane suspension (50 μl). After incubation, the samples are rapidly filtered over glass-fibre mats and the filter mats are washed to remove non-receptor-bound radioligand. Receptor-bound radioligand entrapped on the filter mats is then determined by liquid scintillation counting. Filtration and washing are carried out using a conventional vacuum filtration cell harvester. The specific binding (defined as the difference between the total binding and the non-specific binding) in the presence of the particular test compound is determined and compared with the control value. Results are conveniently expressed as the negative logarithm of the concentration required to cause a 50% displacement of control specific binding ($pIC_{50}$).

In general, compounds of the formula I showing antagonist activity in this assay typically show a $pIC_{50}$ in the above test (a) of 6 or more. Thus for example, the compound of Example 1 herein shows a $pIC_{50}$ of about 7.6. Using the same test procedure, the known compound 1,3-dimethylxanthine typically shows a $pIC_{50}$ of about 5.

(b) Guinea-pig Aortic Constriction Test

This test has been described by Collis et al. (British J. Pharmacology, 1989, 97, 1274-1278) and involves the assessment of the ability of a test compound to antagonise the attenuatory effect of adenosine on phenylephrine induced constriction of a guinea-pig aortic ring preparation, an effect mediated via the adenosine receptor known as $A_2$.

The aortic ring preparation is obtained as follows:
Sections (3-5 mm) of guinea pig thoracic aorta (from Dunkin Hartley strain, 250-400 g males) are mounted in organ baths containing oxygenated Krebs solution (95% $O_2$: 5% $CO_2$) at 37° C. [The nucleoside transport inhibitor, dipyridamole (10 μM) is present in the Krebs solution]. The isometric tension development is recorded and the tissue placed under a resting tension of 1 g and allowed to equilibrate for 1 hour. The aortic ring preparation is then sensitised to $10^{-5}$M phenylephrine. Erythro-9-(2-hydroxy-3-nonyl)adenine (EHNA) (10 μM) is added to the preparation and after 10 minutes the tissue is constricted to approximately 50% maximum by adding $3 \times 10^{-6}$M phenylephrine. Adenosine is next added cumulatively ($10^{-7}$M to $10^{-3}$M) and the evoked relaxation is measured. After washout for 20 minutes, a $10^{-5}$M solution of the test compound in DMSO (maximum 1% by volume) diluted with Krebs solution is added and left to equilibrate for 30 minutes. Twenty minutes into the equilibration period further EHNA (10 μM) is added to the preparation and 10 minutes later phenylephrine ($3 \times 10^{-6}$M) is introduced to produce constrictive tone again. A repeat dose response curve to adenosine is then carried out followed by washout.

Test compounds are assessed by plotting the percentage relaxation observed against the logarithm of the adenosine concentration, competitive adenosine antagonism producing a parallel shift in the standard adenosine concentration/relaxation (dose response) curve. The dose ratio (DR) is calculated from the ratio of the concentration of adenosine to produce a 50% relaxation ($ED_{50}$) in the presence of the test antagonist divided by the $ED_{50}$ concentration of adenosine in the absence of the test antagonist for each aortic ring. Significant antagonist activity in this assay is indicated by a DR of >2. The pA2 value, which is an estimate of the concentration of antagonist to give a dose ratio of 2, may also be calculated using a standard computation technique. Using this test procedure the known compound, 1,3-dimethylxanthine, has a pA2 of about 5.

(c) Guinea-pig Atrial Bradycardic Test

This test has also been described by Collis et al. (*British J. Pharmacology*, 1989, 97, 1274–1278) and involves the ability of a test compound to antagonise the bradycardic effect of the adenosine mimetic, 2-chloroadenosine, in a beating guinea-pig atrial preparation, an effect mediated via the adenosine receptor known as $A_1$.

The atrial pair preparation may be obtained as follows:

Atrial pairs are obtained from guinea-pigs (Dunkin Hartley strain, 250–400 g males) and mounted in organ baths containing oxygenated Krebs buffer solution (95% $O_2$; 5% $CO_2$) at 37° C. The spontaneously beating atria are then placed under a resting tension of 1 g and allowed to equilibrate for 50 minutes with continuous overflow. Overflow is then stopped and adenosine deaminase (1 Unit/ml) added to prevent the accumulation of endogenously produced adenosine. After equilibration for 15 minutes, a cumulative dose response curve to the adenosine mimetic, 2-chloroadenosine ($10^{-8}$M to $10^{-4}$M) is administered to produce a maximal slowing of atrial rate. After washout during 30 minutes, adenosine deaminase is readministered to the bath which is allowed to equilibrate for 15 minutes. A $10^{-5}$M solution of the test compound in DMSO is then added to the bath which is left to incubate for 30 minutes. Any effect on the beating rate due to the test compound is noted before the dose response curve to 2-chloroadenosine is repeated. Compounds which are adenosine antagonists attenuate the 2-chloroadenosine response.

Test compounds are assessed by comparing dose response curves to 2-chloroadenosine alone with those obtained in the presence of the compound. Competitive adenosine antagonists produce a parallel shift in the 2-chloroadenosine dose response curve. The dose ratio (DR) is calculated from the ratio of the concentration of 2-chloroadenosine to produce a 50% reduction in atrial rate ($ED_{50}$) in the presence of the test compound divided by the $ED_{50}$ concentration of 2-chloroadenosine in the absence of the test compound for each atrial pair. The pA2 is then obtained in an analogous manner to that referred to in (b) above. In this test, the compound of Example 1 herein has a pA2 of 7.4. Similarly, the known compound, 1,3-dimethylxanthine, typically shows a pA2 of about 5.

(d) Anaesthetised cat blood pressure Test

This test assesses the ability of a test compound to antagonise the fall in diastolic blood pressure produced by administration of the adenosine mimetic, 2-chloroadenosine.

Male cats (2–3 kg) are anaesthetised with sodium pentobarbitone (45 mg/kg, ip). The following blood vessels are catheterised: right jugular vein (for infusion of the anaesthetic at approximately 7 mg/kg per hour as a 3 mg/ml solution in isotonic saline), the left jugular vein (for administration of test agents) and the right common carotid artery (for monitoring blood pressure and pulse rate). The blood gas status and pH are determined, and are maintained within physiological limits, before administration of 2-chloroadenosine. A control dose response curve (DRC) to 2-chloroadenosine (0.3 to 30 μg/kg) against the fall in diastolic blood pressure is determined. A solution of the test compound in a mixture of 50% v/v polyethylene glycol (PEG) 400 and 0.1M sodium hydroxide is then administered i.v. and after 15 minutes the DRC to 2-chloroadenosine is determined. This procedure is repeated twice with blood gases and pH being monitored and maintained within physiological limits between each DRC. The concentration of 2-chloroadenosine required to cause a 30 mm Hg fall in diastolic blood pressure is then calculated for each dose of test compound and a Schild plot constructed for those which produce a dose ratio (DR) of >2. From this plot a $K_B$ value is determined.

The above Test (d) may conveniently be modified to allow evaluation of orally administered test compounds by administering the test compound to conscious cats with indwelling arterial and venous catheters and measuring the effect in preventing an adenosine induced decrease in blood pressure.

(e) Anaesthetised dog Test

This test involves the assessment of the effects of a test compound on antagonising the actions of adenosine in lowering heart rate and increasing vasodilation (as measured by a fall in hind-limb perfusion pressure).

Beagles (12–18 kg) are anaesthetised with sodium pentobarbitone (50 mg/kg, iv). The following blood vessels are catheterised: right jugular vein (for infusion of the anaesthetic at approximately 112 mg per hour as a 3 mg/ml solution in isotonic saline), right brachial vein (for administration of drugs and test agents), right brachial artery (for measurement of systemic blood pressure and pulse rate) and the left carotid artery (for administration of adenosine into the left ventricle). Both vagi, the right femoral and sciatic nerves are ligated and severed. A bolus injection of 1250 U heparin is administered before perfusing the right hindlimb at constant blood flow with blood from the iliac artery. The right leg is tied just below the ankle. Xamoterol (1 mg/kg) is then administered to the animal to stabilise heart rate at a high level and nitrobenzylthioinosine (NBTI, 0.5 mg/kg) to inhibit the uptake of adenosine. The animal is sensitised to adenosine during the equilibration time following NBTI by carrying out a dose response curve (DRC). During this time any blood gas or pH imbalance is corrected. A control DRC is performed followed by up to three DRC's after cumulative administration of the test compound (as described in (d) above). Each DRC is carried out 15 minutes after administration of test compound and after the measured parameters of heart rate and hindlimb perfusion pressure have returned to a stable state. Similarly, blood gases and pH are maintained within physiological limits throughout the evaluation.

The amount of adenosine required to cause a 50% fall in measured parameter ($ED_{50}$) i.e. heart rate and hindlimb perfusion pressure is calculated for each dose of test compound and a Schild plot constructed. From this plot a $K_B$ value is determined for antagonism of heart rate response and vasodilator response to adenosine.

(f) Anaesthetised cat exercise hyperaemia test

This test involves assessment of the effect of a test compound to antagonise the vasodilation response which occurs during twitch contraction of skeletal muscle. The vasodilation is mediated partly by the release of endogenous adenosine from the contracting skeletal muscle.

Cats (2.4–3.6 kg) are anaesthetised with sodium pentobarbitone (50 mg.kg$^{-1}$ ip). The following blood vessels are catheterized: left jugular vein (for infusion of anaesthetic, at approximately 0.12 mg$^{-1}$min$^{-1}$ as a 6 mg.ml$^{-1}$ solution in isotonic saline), right external jugular vein (for administration of drugs and test compounds), right common carotid artery (for measurement of systemic arterial blood pressure and pulse rate) and right brachial artery (for withdrawal of blood).

Blood flow to the left hind limb is measured with an electromagnetic flow probe around the left external iliac artery. The whole of the left hind limb is made to contract at 3 Hz for 20 minutes duration by stimulating the sciatic and femoral nerves. Active tension produced by the extensor digitorum longus and peroneous longus muscles is measured isometrically with a force transducer. Exercise is repeated twice within the same animal, in either the absence or presence of the test compound. Test compounds are assessed for their ability to reduce the vasodilation during skeletal muscle contraction.

In this test, the known compound, 1,3-dimethylxanthine, produces significant inhibition at 10 mg.kg$^{-1}$.

The compounds of the invention are generally best administered to warm-blooded animals for therapeutic or prophylactic purposes in the treatment or prevention of cardiovascular diseases and adverse conditions in the form of a pharmaceutical composition comprising said compound of formula I or a pharmaceutically acceptable salt thereof, in admixture or together with a pharmaceutically acceptable diluent or carrier. Such compositions are provided as a further feature of the invention.

In general, it is envisaged that a compound of formula I will be administered orally, intravenously or by some other medically acceptable route (such as by inhalation, insufflation, sub-lingual or transdermal means) so that a dose in the general range, for example, 0.001 mg to 10 (and more particularly in the range, for example, 0.05 to 5 mg/kg) mg/kg body weight is received. However, it will be understood that the precise dose administered will necessarily vary according to the nature and severity of the disease or condition being treated and on the age and sex of the patient.

A composition according to the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose from containing, for example, 5–200 mg of the compound of formula I or an equivalent amount of a pharmaceutically acceptable salt thereof.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise the contact of the active ingredient of formula I with stomach acids.

The compositions of the invention may also contain one or more agents known to be of value in the diseases or conditions of the cardiovasculature intended to be treated. Thus, they may contain, in addition to the compound of formula I, for example: a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of new cardiovascular agents in laboratory animals such as cats, dogs, rabbits, monkeys, rats and mice.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet; q,quartet; and (vi) all end-products were characterised by microanalysis, NMR and/or mass spectroscopy.

EXAMPLE 1

To a stirred suspension of magnesium (0.63 g) in ether (10 ml) was added a solution of phenyl bromide (2.7 ml) in ether (20 ml) and the mixture stirred for 1 hour. A solution of 7-amino-2-(2-furyl)-5-methylsulphonyl-[1,2,4]-triazolo[1,3,5]-triazine (1.2 g) in dry tetrahydrofuran (50 ml) was then added at room-temperature and the mixture was stirred for 2 hours. The reaction mixture was then quenched with a saturated aqueous solution of ammonium chloride and the product was extracted with ethyl acetate ($3 \times 100$ ml). The organic solution was dried (magnesium sulphate), filtered and evaporated. The residue was chromatographed on silica-gel eluting with toluene:ethyl acetate (20% v/v) to give a solid, which on crystallisation from isopropanol gave 7-amino-2-(2-furyl)-5-phenyl-[1,2,4]-triazolo[1,5-a][1,3,5]triazine m.p. >300° C.; microanalysis, found: C, 60.6; H, 3.7; N, 29.6% $C_{14}H_{10}N_6O$ requires: C, 60.4; H, 3.7; N, 29.9%; NMR: 6.73 (d of d, 1H, furyl-4H), 7.22 (d, 1H, furyl-3H), 7.55 (complex, 3H, phenyl-3H, phenyl-4H and phenyl-5H), 7.94 (d, 1H, furyl-5H); 8.40 (d of d, 2H, phenyl-2H and phenyl-6H) and 8.93 (d, 2H, $NH_2$); m/e 279 $(M+H)^+$.

The necessary starting material was prepared as follows:

(1) Hydrogen chloride gas (20.0 g) was bubbled into an ice-cooled mixture of 2-furonitrile (46.5 g) and absolute ethanol (23.0 g). After addition of the gas, solid crystallised from the mixture. The crystalline solid was collected by filtration and heated in pyridine (300 ml) with aminoguanidine nitrate (56.0 g) under reflux for 4 hours. The mixture was cooled, solid material removed by filtration and the filtrate evaporated to give crude 3-amino-5-(2-furyl)-1,2,4-triazole. This material was purified by treatment with nitric acid (400 ml of 50% v/v). The crystalline salt which formed was collected by filtration, washed sequentially with water (100 ml) and ethanol (50 ml) and air dried to give 3-amino-5-(2-furyl)-1,2,4-triazole nitrate (45.0 g), m.p. 130°-133° C. (decomp.). Several batches (184.0 g) of this salt (184 g) were suspended in hot water (400 ml) and sodium carbonate (46.0 g) was added in portions. The basic solution obtained was allowed to cool to give 3-amino-5-(2-furyl)-1,2,4-triazole (82.0 g) as colourless prisms, m.p. 204°-206° C.; NMR 6.05(s, 2H, $NH_2$), 6.6(s, 1H, furyl-4H), 6.7(s, 1H, furyl-3H), 7.7(s,1H, furyl-5H), 12.05(br s,1H, NH).

(2) An intimate mixture of 3-amino-5-(2-furyl)-1,2,4-triazole (33.0 g) and dimethyl N-cyanodithioiminocarbonate (33.0 g) was heated at 170° C. for 1 hour, under a slow stream of argon. After cooling, the resulting solid was purified by column chromatography on silica (600 g) eluting with an increasing amount of ethyl acetate in dichloromethane (5–10% v/v) to give 7-amino-2-(2-furyl)-5-methylthio[1,2,4]triazolo[1,5-a][1,3,5-triazine as a colourless solid (11.1 g), essentially pure by TLC, which was used without further purification. [A small amount of the above solid was recrystallised from ethanol to give, crystals, m.p. 238°-240° C.; microanalysis, found: C,44.0; H,3.3; N,33.7; $C_9H_8N_6OS$ 0.05$C_2H_5OH$ requires C,43.6; H,3.3; N,33.6; NMR 1.05 and 3.4 (t+q, ethanol of crystallisation), 2.5 (s, 3H, $CH_3S$—), 6.7(d of d, 1H, furyl-4H), 7.2(d, 1H, furyl-3H), 7.7(d, 1H, furyl-5H) 8.7–9.0(br d, 2H, $NH_2$); m/e 248 $(M+)$.

(3) A solution of 3-chloroperoxybenzoic acid (50% strength, 45.0 g) in dichloromethane (300 ml) was added to a stirred, ice-cooled suspension of 7-amino-2-(2-furyl)-5-methylthio-[1,2,4]triazolo[1,5-a][1,3,5]triazine (8.0 g) in dichloromethane (300 ml). The residual aqueous layer was discarded. The resulting suspension was allowed to warm to ambient temperature and stirred for 16 hours. The solvent was evaporated and ethanol (150 ml) was added to the residue. The suspension obtained was left to stand for 30 minutes with occasional swirling. The solid was then collected by filtration, washed with ethanol and dried to give 7-amino-2-(2-furyl)-5-methylsulphonyl-[1,2,4]triazolo[1,5-a] [1,3,5]triazine (6.6 g) as colourless solid, NMR: 3.3(s, 3H, $CH_3.SO_2$), 6.7(q, 1H, furyl-4H), 7.3(q, 1H, furyl-3H), 7.9(q, 1H, furyl-5H), 9.4–9.8(d, 2H, $NH_2$), which was used without further purification.

EXAMPLE 2

A solution of 2-(2-furyl)-7-methylthio-5-phenylethynyl [1,2,4]-triazolo[1,5-a][1,3,5]triazine (0.8 g) in ethanolic ammonia (40 ml was allowed to stand at ambient temperature for 2 hours. The solvent was then evaporated and the residue was purified by chromatography on silica-gel eluting sequentially with dichloromethane-ethyl acetate (2% v/v) and dichloromethane-methanol (1% v/v) to give a solid (0.25 g). This was crystallised from isopropanol (50 ml) and gave 7-amino-2-(2-furyl)-5-phenylethynyl-[1,2,4]triazolo[1,5-a] [1,3,5]triazine as colourless crystals mp >280° C.; microanalysis, found: C, 62.9; H, 4.2, N, 24.9%; $C_{16}H_{10}N_6O$ (0.5) $C_3H_7OH$ requires: C, 63,2; H, 4.2; N, 25.3%; NMR 6.74 (d of d, 1H, furyl-4H; 7.24 (d of d, 1H, furyl-3H); 7.53 (complex, 3H, phenyl-3H, phenyl-4H and phenyl-5H) 7.68 (complex, 2H, phenyl-2H and phenyl-6H, 7.95 (m, 1H, furyl-5H) and 9.07 (br s, 2H, $NH_2$); m/e 381 $(M+H)^+$.

The starting material was prepared as follows:

(a) To a solution of 2-(2-furyl)-5-iodo-7-methylthio-[1,2,4]triazolo[1,5-a][1,3,5]triazine (2.5 g) and phenyl acetylene (1.5 ml) in dimethylformamide (40 ml) was added triethylamine (1.1 ml), bis(triphenylphosphine)-palladium (II) chloride (0.2 g) and cuprous iodide (0.1 g) and the mixture stirred at room- temperature for 3 hours. The reaction mixture was diluted with water (350 ml) and extracted with ethyl acetate ($3 \times 50$ ml). The organic extract was washed with water, dried magnesium sulphate and evaporated. The crude product was purified by chromatography on silica-gel (150 g), eluting with ethyl acetate dichloromethane (1% v/v). The residue from the fractions containing the product were triturated with ether and filtered to give 2-(2-furyl)-7-methylthio-5-phenylethynyl-[1,2,4]-triazolo[1,5-a][1,3,5]triazine (1.0 g). Crystallisation of an aliquot from isopropanol gave a yellow crystalline product m.p. 188°-190° C.; microanalysis, found: C, 60.8; H, 3.1; N, 20.9%, $C_{17}H_{11}N_5OS$ requires C, 61.2; H, 3.3; N,21.0%; NMR 2.8 (S, 3H, $CH_3S$); 6.75 (d of d, 1H, furyl-4H); 7.35 (d, 1H, furyl-3H), 7.55 (complex, 3H, phenyl-3H, phenyl-4H and phenyl-5H), 7.74 (complex, 2H, phenyl-2H and phenyl-6H) and 8.0 (d, 1H, furyl-5H); m/e 353$M^+$.

(b) A mixture of 5-amino-2-(2-furyl)-7-methylthio-[1,2,4]triazolo[1,5-a][1,3,5]triazine (5 g), diiodo methane (40 ml) and amyl nitrite (8 ml) was stirred at 120° C. for 75 minutes. The reaction mixture was filtered through silica-gel (250 g) using dichloromethane as solvent and the residual 2-(2-furyl)-5-iodo-7-methylthio-[1,2,4]triazolo[1,5-a][1,3,5]triazine was used directly. An aliquot was crystallised from toluene and gave a pale yellow solid m.p. 211°-213° C.; NMR 2.73 (s, 3H, CH$_3$S), 6.74 (d of d, 1H, furyl-4H), 7.33 (d, 1H, furyl-3H) and 7.98 (d, 1H, furyl-5H), m/e 360 (M+H)$^+$.

(c) An itimate mixture of 3-amino-5-(2-furyl)-[1,2,4]triazole (15 g) and dimethyl N-cyanodithioiminocarbonate (16 g) was heated at 170° C. for 50 minutes under a slow stream of argon. After cooling, the resulting solid was triturated with methanol and filtered to afford 7-amino-2-(2-furyl)-5-methylthio[1,2,4]-triazolo[1,5-a][1,3,5]triazine as a yellow-green solid. The residue from the filtrate was chromatographed on silica gel, eluting with dichloromethane-methanol 97.5/2.5 v/v to give further 7-amino-2-(2-furyl)-5-methylthio[1,2,4]triazolo[1,5-a][1,3,5]triazine (4.4 g) followed by 5-amino-2-(2-furyl)-7-methylthio-[1,2,4]triazolo[1,5-a][1,3,5]triazine (2.2 g) as a yellow solid. A small amount of the above solid was crystallised from methanol and gave pale yellow needles, m.p. 254°–7° C.; microanalysis, found: C, 43.0; H, 3.5; N, 33.4; S 12.4%; C$_9$H$_8$N$_6$OS (0.125)CH$_3$OH requires: C, 43.4, H, 3.6; N, 33.3; S, 12.7%; NMR: 2.67 (s, 3H, CH$_3$S), 6.68 (d of d, 1H, furyl-4H), 7.15 (d, 1H, furyl-3H); 7.68 (br s, 2H, NH$_2$) and 7.89 (d, 1H, furyl-5H); m/e 248 (M$^+$).

5-Iodo-7-methylthio-2-(2-furyl)-[1,2,4]triazolo[1,5-a][1,3,5]triazine may also be prepared as follows:

A mixture of 5-amino-2-(2-furyl)-7-methylthio-[1,2,4]triazolo-[1,5-a][1,3,5]triazine (5.95 g), iodine (6.07 g), cuprous iodide (4.85 g), di-iodomethane (15 ml), isopentylnitrite (10 ml) in tetrahydrofuran (120 ml) was stirred at reflux under an argon atmosphere for 2 hours. The mixture was cooled, filtered through diatomaceous earth and evaporated. The residual oil was dissolved in dichloromethane (200 ml), washed with sodium thiosulphate solution to remove unreacted iodine, filtered through phase separating paper and evaporated to give a brown oil (5.5 g) which was purified by chromatography on silica gel (200 g), using 1% methanol in dichloromethane as eluant, to afford a solid (3.5 g). Recrystallistion of this solid from ethanol gave 5-iodo-7-methylthio-2-(2-furyl)[1,2,4]triazolo[1,5-a][1,3,5]triazine (1.6 g).

EXAMPLE 3

A solution of the product of Example 2 (0.17 g) in ethanol (150 ml) was hydrogenated at room temperature and pressure using 10% palladium on carbon (0.19 g) catalyst. After the uptake of the hydrogen was complete, the catalyst was filtered off and the solvent evaporated. The residue was crystallised from isopropanol and gave 7-amino-2-(2-furyl)-5-[(2-phenyl)ethyl]-[1,2,4]-triazolo[1,5-a][1,3,5]triazine m.p. 235°–237° C. microanalysis, found: C,62.2; H, 4.6; N,27.3%, C$_{16}$H$_{14}$N$_6$O requires: C,62.7; H,4.6; N,27.4%; NMR 2.98 (m, 2H, CH$_2$), 3.07(m, 2H, CH$_2$), 6.71(d, 1H, furyl-4H), 7.16(m, furyl-3H), 7.1–7.3(complex, 5H, phenyl-H), 7.93(s, 1H, furyl-5H) and 8.84(br d, 2H, NH$_2$).

EXAMPLE 4

Using a similar procedure to that described in Example 1 but using 3-trifluoromethyl bromobenzene; there was obtained 7-amino-2-(2-furyl)-5-[3-trifluoromethyl-phenyl]-[1,2,4]-triazolo[1,5-a][1,3,5]triazine m.p. 296°–8° C.; microanalysis, found: C, 51.8; H,2.6; N, 24.0% C$_{15}$H$_9$F$_3$N$_6$O requires: C, 52.0; H,2.6; N, 24.3%, NMR: 6.74(d of d, 1H, furyl-4H), 7.23(d, 1H, furyl-3H), 7.61(t, 1H, phenyl-5H), 7.96(complex, 2H, furyl-5H and phenyl-4H), 8.66 (s and d, 2H, phenyl-6H and phenyl 2H), 9.07(d, 2H, NH$_2$); m/e 347 (M+H)$^+$.

EXAMPLE 5

Using a similar procedure to that described in Example 1 but using 4-methoxy bromobenzene; there was obtained 7-amino-2-(2-furyl)-5-[4-methoxyphenyl]-[1,2,4]-triazolo[1,5-a][1,3,5]triazine m.p. >275° C.; microanalysis, found: C, 58.3; H, 3.9; N, 26.9% C$_{15}$H$_{12}$N$_6$O$_2$ requires: C, 58.4; H, 3.9; N, 27.3%; NMR: 3.86(s, 3H, CH$_3$O), 6.73(d of d, 1H, furyl-4H), 7.08 and 8.35(A$_2$B$_2$ pattern, 4H, phenyl-H), 7.20(d, 1H, furyl-3H), 7.94(d, 1H, furyl-5H) and 8.85(d, 2H, NH$_2$); m/e 309(M+H)$^+$.

EXAMPLE 6

Using a similar procedure to that described in Example 1 but using 4-methyl-bromobenzene; there was obtained 7-amino-2-(2-furyl)-5-[4-methylphenyl]-[1,2,4]-triazolo[1,5-a][1,3,5]triazine m.p. >275° C.; microanalysis, found C,61.8; H,4.2; N,28.6% C$_{15}$H$_{12}$N$_6$O requires: C, 61.6; H, 4.1; N, 28.8%; NMR: 6.73(d of d, 1H, furyl-4H), 7.21(d, 1H, furyl-3H) 7.35 and 8.29(A$_2$B$_2$ pattern, 4H, phenyl-H), 7.94(d, 1H, furyl-5H) and 8.88(d, 2H, NH$_2$); m/e 293(M+H)$^+$.

EXAMPLE 7

Using a similar procedure to that described in Example 1 but using 3-fluoro bromobenzene; there was obtained 7-amino-5-[3-fluorophenyl]-2-(2-furyl)-[1,2,4]-triazolo[1,5-a][1,3,5]triazine m.p. >300° C.; microanalysis, found: C, 56.8; H, 2.9; N, 28.2%; C$_{14}$H$_9$FN$_6$O requires C, 56.8; H, 3.1; N, 28.4%; NMR: 6.73(d of d, 1H, furyl-4H), 7.23(d of d, 1H, furyl-3H), 7.44(complex t, 1H, phenyl-4H), 7.60(complex, 1H, phenyl-5H), 7.95(d, 1H, furyl-5H), 8.09 and 8.24 (complex d, phenyl-2H and phenyl-6H) and 9.00 (d, 2H, NH$_2$); m/e 297 (M+H)$^+$.

EXAMPLE 8

Using a similar procedure to that described in Example 1 but using 3,5-difluorobromobenzene; there was obtained 7-amino-5-[3,5-difluorophenyl]-2-(2-furyl)-[1,2,4]-triazolo[1,5-a][1,3,5]triazine m.p. 356°–60° C.; microanalysis, found: C, 53.6; H, 2.4; N, 26.7%; C$_{14}$H$_8$F$_2$N$_6$O requires: C, 53.5; H, 2.6; N, 26.7%; NMR: 6.74 (d of d, 1H, furyl-4H), 7.23(d, 1H, furyl-3H), 7.48 (t of t, 1H, phenyl-4H), 7.95 (complex, 3H, furyl-5H, phenyl-2H and phenyl 6-H) and 9.07 (d, 2H, NH$_2$); m/e 315 (M+H)$^+$.

EXAMPLE 9

Using a similar procedure to that described in Example 1 but using 2-bromothiophene; there was obtained 7-amino-2-(2-furyl)-5-(2-thienyl)-[1,2,4]-triazolo[1,5-a][1,3,5]triazine m.p. 324°–8° C. (decomp); microanalysis, found: C, 50.9; H, 2.8; N, 29.3% C$_{12}$H$_8$N$_6$OS requires C, 50.7; H, 2.8; N, 29.6%; NMR: 6.73 (d of d, 1H, furyl-4H), 7.21 (d, 1H, thienyl-4H), 7.23 (d, 1H, furyl-3H), 7.64 (d of d, 1H, thienyl-5H), 7.95 (complex, 2H, furyl-5H and thienyl-3H) and 8.94 (d, 2H, NH$_2$); m/e 285 (M+H)$^+$.

EXAMPLE 10

Using a similar procedure to that described in Example 1 but using 4-benzyloxybenzyl chloride; there was obtained 7-amino-5-[4-benzyloxybenzyl]-2-(2-furyl)[1,2,4]triazolo[1,5-a][1,3,5]triazine m.p. 220°–2° C., microanalysis, found: C, 65.7; H, 4.5; N, 20.8; H$_2$O, 0.7% C$_{22}$H$_{18}$N$_6$O$_2$ (0.15)H$_2$O requires C, 65.9; H, 4.6; H, 20.95; H$_2$O 0.7%; NMR: 3.91 (s, 2H, CH$_2$), 5.07 (s, 2H, CH₂O), 6.70 (d of d, 1H, furyl-4H), 6.93 and 7.25 (A₂B₂ pattern, 4H, phenyl-H), 7.16 (d, 1H, furyl-3H), 7.3-7.5 (complex, 5H, phenyl-H), 7.92 (d, 1H, furyl-5H) and 8.8 (d, 2H, NH₂); m/e 399 (M+H)⁺.

EXAMPLE 11

Using a similar procedure to that described in Example 1 but using 3-trifluoromethyl-bromobenzene; there was thus obtained 7-amino-2-(2-furyl)-5-[3-trifluoromethylphenyl]pyrazolo[2,3-a][1,3,5]triazine m.p. 252°-4° C.; microanalysis, found: C, 55.4; H, 2.9; N, 20.3% C₁₆H₁₀F₃N₅O requires C, 55.7; H, 2.9; N, 20.3%; NMR: 6.70 (d of d, 1H, furyl-4H), 6.81 (s, 1H, pyrazole-3H), 7.09 (d of d, 1H, furyl-3H), 7.77 (t, 1H, phenyl-5H), 7.88 (complex, 2H, furyl-5H and phenyl-4H), 8.64 (complex, 2H, phenyl-6H and phenyl-2H) and 8.70 (d, 2H, NH₂); m/e 346(M+H)⁺.

EXAMPLE 12

Using a similar procedure to that described in Example 1 but using 1-bromo-3-phenylpropane; there was obtained 7-amino-2-(2-furyl)-5-[3-phenylpropyl]-[1,2,4]-triazolo[1,5-a][1,3,5]triazine m.p. 164°-7° C., microanalysis, found: C, 64.0; H, 5.1, N, 26.3% C₁₇H₁₆N₆O requires C, 63.7; H, 5.0; N, 26.2% NMR: 2.05 (quintet, 2H, CH₂CH₂CH₂), 2.68 (complex, 4H, aryl-CH₂), 6.73 (d of d, 1H, furyl-4H), 7.1-7.4 (complex, 6H, phenyl-H and furyl-3H), 7.94 (d, 1H, furyl-5H) and 8.8 (d, 2H, NH₂); m/e 321 (M+H)⁺.

EXAMPLE 13

Using a similar procedure to that described in Example 1 but forming the hexyne-Grignard reagent by metal exchange between hex-1-yne and an ethyl-Grignard reagent; there was obtained 7-amino-2-(2-furyl)-5-[hex-1-ynyl]-[1,2,4]triazolo[1,5-a][1,3,5]-triazine m.p. 188°-91° C.; microanalysis, found: C, 59.1; H, 5.0, N, 29.8; H₂O, 0.4% C₁₄H₁₄N₆O (0.1)H₂O requires C, 59.1; H, 5.0; N, 29.6; H₂O, 0.6%; NMR 0.93 (t, 3H, CH₃), 1.3-1.65 (complex, 4H, —CH₂CH₂—), 2.50 (complex, CH₂C≡), 6.73 (d of d, 1H, furyl-4H), 7.23 (d, 1H, furyl-3H), 7.95 (d, 1H, furyl-5H) and 8.95 (d, 2H, NH₂); m/e 283 (M+H)⁺.

EXAMPLE 14

A solution of 7-amino-2-(2-furyl)-5-[4-methoxyphenyl][1,2,4]triazolo[1,5-a][1,3,5]triazine (0.23 g) in acetic anhydride (10 ml) was heated on the steam-bath for 18 hours. The solvent was then evaporated in vacuo and the residue was purified by chromatography on silica-gel eluting with dichloromethane containing ethyl acetate (5% v/v). The solid obtained from the chromatography was crystallised from ethanol and gave 7-acetylamino-2-(2-furyl)-5-[4-methoxyphenyl][1,2,4]-triazolo[1,5-a][1,3,5]triazine m.p. 243°-6° C.; microanalysis, found: C, 58.0; H, 4.0; N, 23.9% C₁₇H₁₄N₆O₃ requires C, 58.3; H, 4.0; N, 24.0%; NMR 2.50 (s, NHCOCH₃), 3.87 (s, 3H, CH₃O), 6.75 (d of d, 1H, furyl-4H), 7.12 and 8.42 (A₂B₂ pattern, 4H, phenyl-H), 7.32 (d, 1H, furyl-3H), 7.98 (d, 1H, furyl-5H) and 11.42 (s, H, NHCOCH); m/e 351 (M+H)⁺.

EXAMPLE 15

Using a similar procedure to that described in Example 1 but using 4-bromo-1-butene; there was obtained 7-amino-5-(but-3-enyl)-2-(2-furyl)-[1,2,4]triazolo[1,5-a][1,3,5]triazine m.p. 194°-6° C.; microanalysis, found: C, 55.8; H, 5.3; N, 30.6% C₁₂H₁₂N₆O (0.4)C₂H₅OH C, 56.0; H, 5.3; N, 30.6%; NMR 2.77 (t, 2H, CH₂CH=), 3.46 (t, CH₂), 4.9-5.15 (complex, 2H, CH₂=), 5.9 (m, 1H, CH=), 6.71 (d of d, 1H, furyl-4H), 7.17 (d, 1H, furyl-3H), 7.92 (d, 1H, furyl-5H); and 8.8 (d, 2H, NH₂); m/e 257 (M+H)⁺.

EXAMPLE 16

Using a similar procedure to that described in Example 1 but using bromohexane; there was obtained 7-amino-2-(2-furyl)-5-hexyl[1,2,4]triazolo[1,5-a][1,3,5]triazine m.p. 131°-3° C. microanalysis, found: C, 58.7; H, 6.3; N, 29.3% C₁₄H₁₈N₆O requires C, 58.7; H, 6.3; N, 29.3%; NMR: 0.86 (t, 3H, CH₃), 1.29 (m, 4H, CH₃CH₂CH₂), 1.73 (m, 2H, βCH2), 2.65 (t, 2H, αCH₂), 6.71 (d of d, 1H, furyl-4H), 7.17 (d, 1H, furyl-3H), 7.92 (d, 1H, furyl-5H) and 8.77 (d, 1H, furyl-5H), m/e 287 (M+H)⁺.

EXAMPLE 17

Sodium hydride (86 mg of a 50% dispersion in oil) was added to a stirred solution of 7-amino-5-[3,5-difluorophenyl]-2-(2-furyl)-1,2,4-triazolo[1,5-a][1,3,5]triazine (0.421 g) in dimethylformamide (5 ml). The mixture was stirred until the effervesence had ceased and a clear solution was obtained. Iodomethane (0.256 g, 0.11 ml) was then added and the reaction mixture was stirred at ambient temperature for 2 hours. Water (25 ml) and glacial acetic (0.5 ml) were then added and the resulting aqueous suspension was extracted with ethyl acetate (3×50 ml). The organic extracts were combined and washed with water (2×25 ml) and brine (25 ml), dried (MgSO₄) and evaporated to give a yellow solid. This was purified by chromatography on silica. Elution with toluene containing ethyl acetate (10% v/v) gave 5-[3,5-difluorophenyl]-2-(2-furyl)-7-methylamino-[1,2,4]triazolo[1,5-a][1,3,5]triazine as a white solid m.p. 231°-4° C. microanalysis, found: C, 55.0; H, 3.1; N, 25.5% C₁₅H₁₀F₂N₆O requires C₁₅H₁₀F₂N₆O C, 54.9; H, 3.1; N, 25.6%; NMR 3.16 (s, 3H, CH₃N), 6.73 (d of d, 1H, furyl-4H), 7.21 (d of d, 1H, furyl-3H), 7.47 (t of t, 1H, phenyl-4H), 7.93 (d, 1H, furyl-5H), 7.97-8.05 (complex, 2H, phenyl-2H and phenyl-6H) and 9.31 (s, 1H, NH); m/e 329 (M+H)⁺.

EXAMPLE 18

The following illustrate representative pharmaceutical dosage forms containing a compound of formula I, for example as illustrated in any of the previous Examples, (hereafter referred to as "compound X"), for therapeutic or prophylactic use in humans:

| (a) Tablet | mg/tablet |
| --- | --- |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (b) Capsule | mg/capsule |
| --- | --- |
| Compound X | 10 |
| Lactose Ph. Eur | 488.5 |
| Magnesium stearate | 1.5 |

The above formulations may be obtained by conventional procedures well known in the pharmaceutical art. The tablets may be enteric coated by conventional means, for example to provide a coating of cellulose acetate phthalate.

CHEMICAL FORMULAE

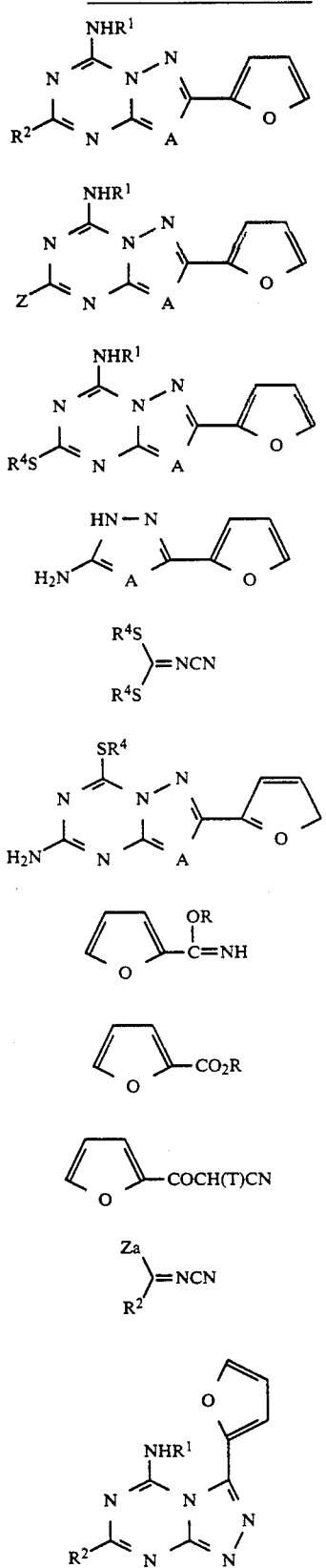

-continued
CHEMICAL FORMULAE

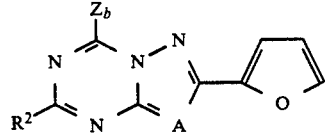

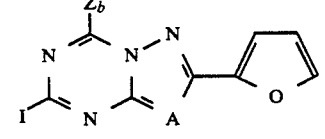

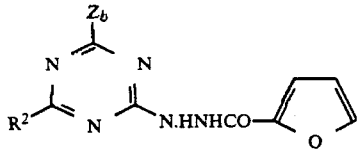

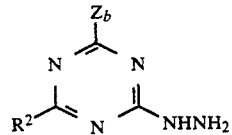

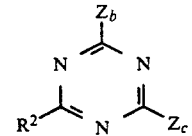

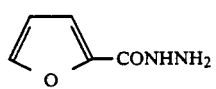

What is claimed is:

1. A compound of the formula I:

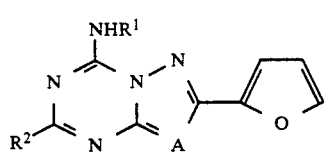

wherein
$R^1$ is hydrogen, (1–6C)alkyl, or (1–4C)alkanoyl;
$R^2$ is phenyl, a C-linked aromatic 5- or 6-membered heterocyclic ring which is selected from the group consisting of thienyl, furyl, pyridyl, and thiazolyl, or (1–8C)alkyl, alkenyl or alkynyl unsubstituted or substituted by a phenyl or C-linked aromatic 5- or 6-membered heterocyclic ring which is selected from the group consisting of thienyl, furyl, pyridyl, and thiazolyl, any phenyl being unsubstituted or substituted by one, two or three of (1–4C)alkyl, (1–4C)alkoxy, halogen, trifluoromethyl, hydroxy, benzyloxy and (1–5C)alkanoyloxy;
A is N or CT in which T is hydrogen or (1–4C)alkyl;
or a pharmaceutically acceptable salt thereof.

2. A compound as claimed in claim 1, in which $R^1$ is hydrogen, methyl or acetyl.

3. A compound as claimed in claim 1 or claim 2, in which $R^2$ is a group of formula $R^3(CH_2)_nX_m$ in which n is 0 or an integer of from 1 to 6; m is 0 or 1; X is HC=CH or C≡C; and $R^3$ is phenyl unsubstituted or substituted by one, two or three of (1-4C)alkyl, (1-4C)alkoxy, halogen, trifluoromethyl, hydroxy, benzyloxy and (1-5C)alkanoyloxy, or a C-linked aromatic 5- or 6-membered heterocyclic ring which is selected from the group consisting of thienyl, furyl, pyridyl, and thiazolyl, or when n is greater than 0, hydrogen.

4. A compound as claimed in claim 1 or claim 2 in which the possible substituents on phenyl are selected from methyl, ethyl, methoxy, ethoxy, fluorine, chlorine, trifluoromethyl, hydroxy, benzyloxy and pivaloyloxy.

5. A compound as claimed in claim 1 or claim 2, in which A is N or CH.

6. A pharmaceutical composition, which comprises an effective amount of a compound of formula I or a pharmaceutically acceptable salt thereof, as claimed in claim 1, in admixture or together with a pharmaceutically acceptable diluent or carrier.

7. A method of antagonising one or more of the action of adenosine in a warm-blooded mammal requiring such treatment by administering an effective amount of a compound of formula I as defined in claim 1, or a pharmaceutically acceptable salt thereof.

8. A compound of formula XII:

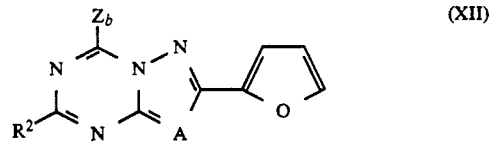

in which $R^2$ is phenyl, a C-linked aromatic 5- or 6-membered heterocyclic ring which is selected from the group consisting of thienyl, furyl, pyridyl, and thiazolyl, or (1-8C)alkyl, alkenyl or alkynyl unsubstituted or substituted by a phenyl or C-linked aromatic 5- or 6-membered heterocyclic ring which is selected from the group consisting of thienyl, furyl, pyridyl, and thiazolyl, any phenyl being unsubstituted or substituted by one, two or three of (1-4C)alkyl, (1-4C)alkoxy, halogen, trifluoromethyl, hydroxy, benzyloxy and (1-5C)alkanoyloxy; and $Z_b$ is a leaving group selected from aryloxy, alkylthio and halogeno.

* * * * *

UNITED STATES PATENT AND TRADEMARK OFFICE
CERTIFICATE OF CORRECTION

PATENT NO. : 5,290,776
DATED : March 1, 1994
INVENTOR(S) : CAULKETT et al.

It is certified that error appears in the above-indentified patent and that said Letters Patent is hereby corrected as shown below:

```
        On the title page, change
"[30] Priority Application Priority Data
 Jun. 23, 1991 [GB] United Kingdom
 ......9111130"
to
--[30] Priority Application Priority Data
  May 23, 1991 [GB] United Kingdom
  ......9111130.2--.
```

Signed and Sealed this

Eleventh Day of October, 1994

Attest:

BRUCE LEHMAN

*Attesting Officer*         *Commissioner of Patents and Trademarks*